United States Patent [19]

Haub et al.

[11] Patent Number: 4,959,549
[45] Date of Patent: Sep. 25, 1990

[54] DETERMINATION OF PROPERTIES OF COAL

[75] Inventors: John G. Haub, Wentworthville; John E. Eberhardt, Sans Souci; David L. Death, Bankstown, all of Australia

[73] Assignee: Commonwealth Scientific and Industrial Research Organisation, Campbell, Australia

[21] Appl. No.: 339,926

[22] Filed: Apr. 17, 1989

Related U.S. Application Data

[63] Continuation of Ser. No. 126,914, Nov. 27, 1987, abandoned.

[30] Foreign Application Priority Data

Nov. 28, 1986 [AU] Australia ............... PH9237

[51] Int. Cl.$^5$ ............... G01N 21/64; G01N 21/63; G01N 21/85
[52] U.S. Cl. ............... 250/461.1; 250/459.1; 250/358.1; 250/359.1; 250/360.1
[58] Field of Search ............... 250/461.1, 459.1, 458.1, 250/358.1, 359.1, 360.1

[56] References Cited

U.S. PATENT DOCUMENTS

| | | | |
|---|---|---|---|
| 2,346,481 | 4/1944 | Garrison | 250/461.1 |
| 4,200,801 | 4/1980 | Schuresko | 250/458.1 |
| 4,228,353 | 10/1981 | Johnson | 250/356.1 |
| 4,365,153 | 12/1982 | Seigel et al. | 250/461.1 |
| 4,491,411 | 1/1985 | Goldstein | 250/253 |
| 4,577,109 | 3/1986 | Hirschfeld | 250/461.1 |
| 4,591,718 | 5/1986 | Amer | 250/339 |
| 4,613,237 | 9/1986 | Melton | 250/459.1 |
| 4,616,133 | 10/1986 | Senftle | 250/461.1 |
| 4,626,693 | 12/1986 | Hirschfeld | 250/461.1 |
| 4,798,463 | 1/1989 | Koshi | 250/458.1 |
| 4,814,614 | 3/1989 | Tsui | 250/461.1 |

FOREIGN PATENT DOCUMENTS 79777 5/1982 Australia .

OTHER PUBLICATIONS

Brown et al., "Fluorescent Line Narrowing Spectrometry in Glases for Direct Determination of Polycyclic Aromatic Hydrocarbons in Solvent-Refined Coal", *Analytical Chemistry*, vol. 52, No. 11, 9/1980, pp. 1711–1715.

(List continued on next page.)

*Primary Examiner*—Constantine Hannaher
*Assistant Examiner*—Jacob M. Eisenberg
*Attorney, Agent, or Firm*—Ladas & Parry

[57] ABSTRACT

Methods and apparatus for determining a property of bulk coal from a fluorescence spectrum of the coal are disclosed. In the methods the coal is illuminated so that a plurality of macerals at the surface of the coal are illuminated with UV light. Intensities of fluorescent light from the coal are determined as a function of wavelength and output signals related to the intensities are derived as a function of wavelength. A property of the bulk coal is then determined by:

(A)
(i) determining amplitudes related to the intensities, of the output signals as a function of wavelength:
(ii) integrating the amplitudes within a selected wavelength region to provide at least one integrated value:
(iii) compring the integrated value with at least one standard integrated value derived from the calibration study of coal; and
(iv) ccalculating quantitatively the property of the bulk coal from the comparison; or (B)
(i) determining amplitudes related to the intensities, of the output signals as a function of wavelength;
(ii) ratioing the amplitudes within a first selected wavelength region with the amplitudes within a second selected wavelength region to provide a ratioed value;
(iii) comparing the ratioed value with at least one standard ratioed value derived from the calibration study of coal; and
(iv) calculating quantitatively the property of the bulk coal from the comparison.

41 Claims, 18 Drawing Sheets

OTHER PUBLICATIONS

Australian Standard 1038-5.1 (1988) "Methods for the Analysis and Testing of Coal and COle Part 5.1—Gross Specific Energy of Coal and Coke—Adiabatic Calorimeters".
Australian Standard 2646.1 (1984) "Sampling of Solid Mineral Fuels Part 1—Guide to the use of Parts 2 to 8".
Australian Standard 2646.2 (1984) "Sampling of Solid Mineral Fuels Part 2—Hard Coal—Sampling from Moving Streams".
Australian Standard 2646.3 (1985) "Sampling of Solid Mineral Fuels Part 3—Coke—Sampling from Moving Streams".
Australian Standard 2646.4 (1984) "Sampling of SOlid Mineral Fuels Part 4—Hard Coal—Sampling from Stationary Situations".
Australian Standard 2646.5 (1985) "Sampling of Solid Mineral Fuels Part 5—Coke—Sampling from Stationary Situations".
Australian Standard 2646.6 (1984) "Sampling of SOlid Mineral Fuels Part 6—Hard Coal'Preparation of Samples".
Australian Standard 2646.7 (1984) "Sampling of Solid Mineral Fuels Part 7—Coke—Preparation of Samples".
Australian Standard 2646.8 (1984) "Sampling of SOlid Mineral Fuels Part 8—Determination of Precision and Bias".
Australian Standard 1038.1 (1980) "Methods for the Analysis and Testing of Coal and Coke Part 1—Total Moisture in Hard Coal".
Australian Standard 1038.2 (1979) "Methods for the Analysis and Testing of Coal and COke Part 2—Total Moisture in Coke".
Australian Standard 1038.3 (1979) "Methods for the Analysis and Testing of Coal and Coke Part 3—Proximate Analysis of Hard Coal".
Australian Standard 1038.4 (1979) "Method for the Analysis and Testing of Coal and Coke Part 4—Proximate Analysis of Coke".
Australian Standard 1038.5 (1979) "Methods for the Analysis and Testing of Coal and Coke Part 5—Gross Specific Energy of Coal and Coke".
Australian Standard 1038-6.1 (1986) "Methods for the Analysis and Testing of Coal and Coke Part 6.1—Ultimate Analysis of Higher Rank Coal—Determination of Carbon and Hydrogen".
Australian Standard 1038-6.2 (1986) "Methods for the Analysis and Testing of Coal and Coke Part 6.2—Ultimate Analysis of Higher Rank Coal—Determination of Nitrogen".
Australian Standrad 1038-6.3.1 (1986) "Methods for the Analysis of Higher Rank Coal—Determination of Total Sulphur (Eschka Method)".
Australian standard 1038-6.3.2 (1986) "Methods for the Analysis and Testing of Coal and Coke Part 6.3.2—Ultimate Analysis of Higher rank Coal—Determination of Coal Sulphur (High Temperature Combustion Method)".
Australian Standard 1038-6.3.3 (1986) "Methods for the Analysis and Testing of Coal and Coke Part 6.3.3—Ultimate Analysis of Higher Rank Coal—Determination of Total Sulphur (Infrared Method)".
Australian Standard 2137 (1981) "Hard Coal—Determination of Plastic Properties by the Gieseler Plastometer".
Australian Standard 2486 (1981) "Microscopical Determination of the Reflectance of Coal Marcerals".
"Coal Structure" Edited by Robert A Meyers (1982) Academic Press Chapter 2 "Coal Macerals" Francis T C Ting.
M. Teichmuller and B. Durand, Int. J. of Coal Geology, 2(1983) 197—230.
J.C. Crelling and D. F. Bensley, "Characterization . . . Macerals" ACS Symposium Series 252 Ed. R. E. Winans et al., American Chemical Society, 198.

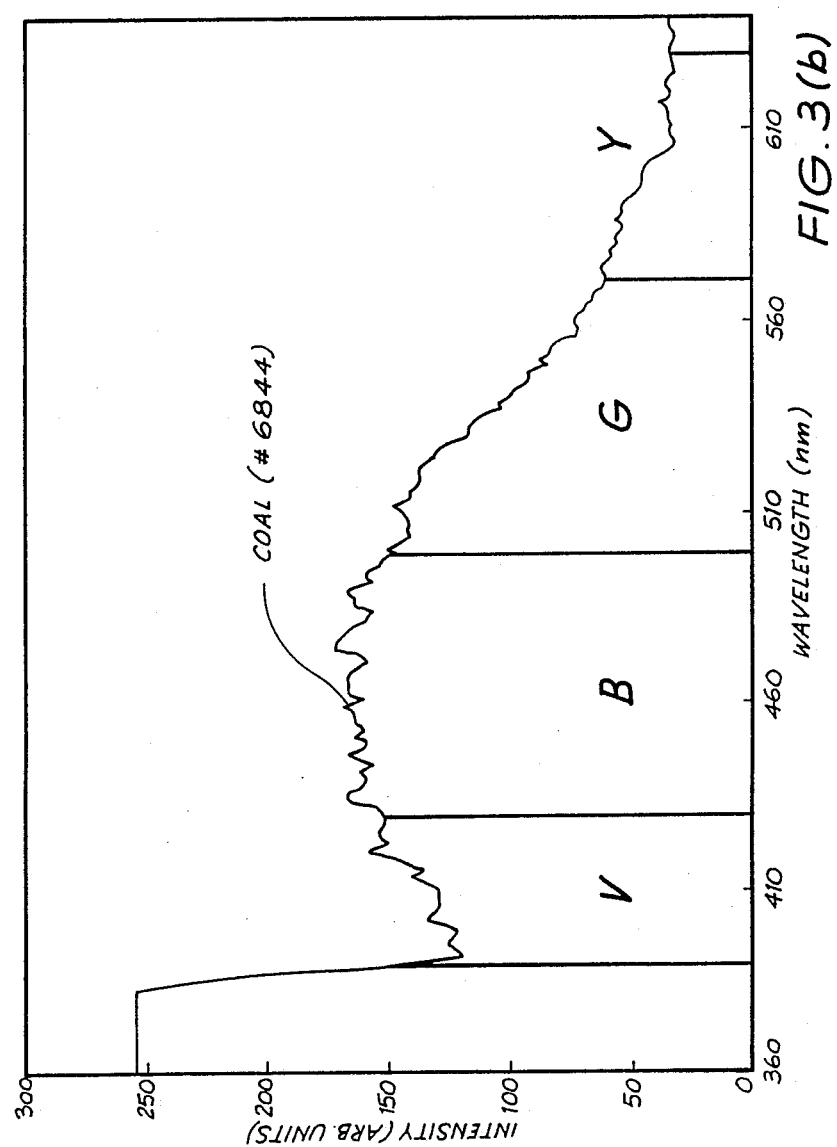

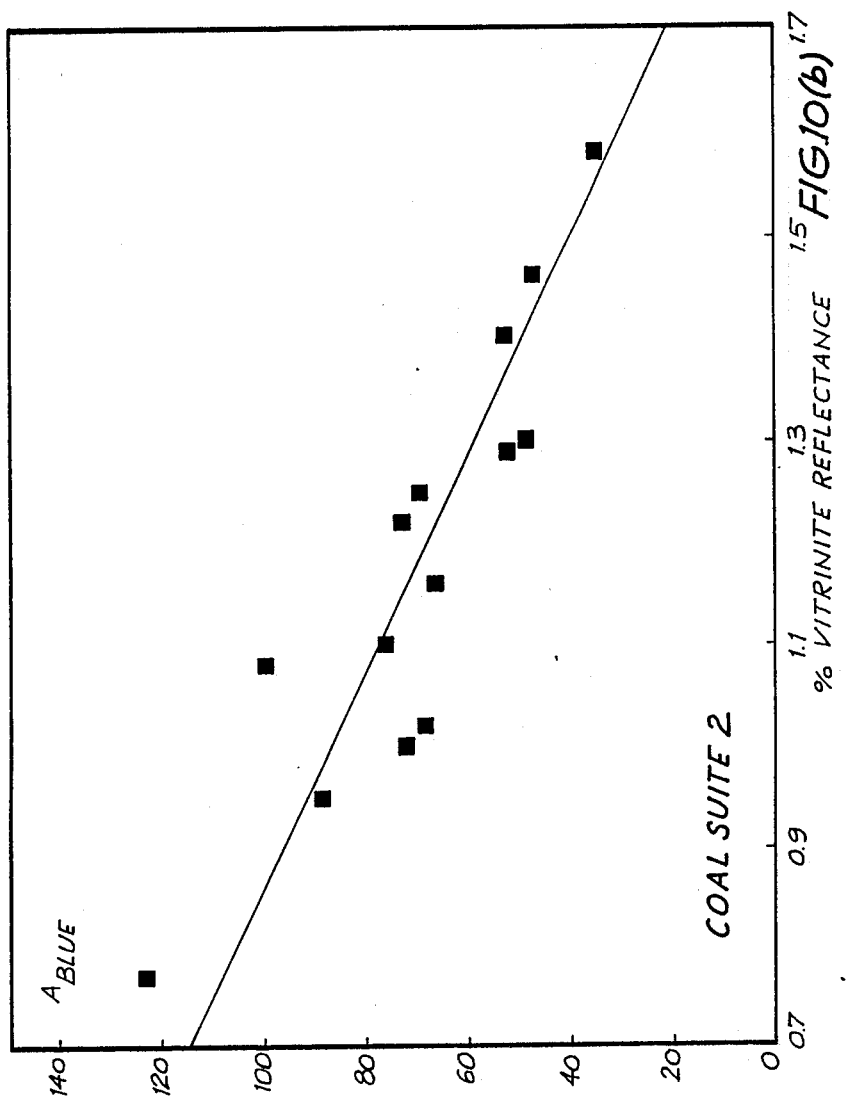

DETERMINATION OF PROPERTIES OF COAL

This is a continuation of application Ser. No. 126,914 filed on Nov. 27, 1987, now abandoned.

This invention relates to an apparatus for providing an output signal which is quantitatively related to a property of bulk coal and a method for quantitatively measuring a property of bulk coal. As used throughout the specification and claims a reference to coal also includes a reference to coke.

This invention also relates to an apparatus and method for characterising bulk coal by measuring the variation of the fluorescent spectrum thereof.

Both the spectral distribution and intensity at certain wavelengths change with maturity of the coal. Properties which can be measured by the apparatus and method of this invention include rank, vitrinite, reflectance, atomic H/C ratio, carbon, hydrogen and volatile contents, degree of surface oxidation, calorific value, coke yield, Gieseler initial softening temperature, Gieseler resolidification temperature, Gieseler maximum fluidity temperature and Dilatometer maximum dilatation temperature [Standards Association of Australia, "Determination of the Dilatometer characteristics of higher rank coals", AS 1038 part 12.3 (1984), and "Hard coal-determination of plastic properties by the Gieseler plastometer", AS 2137 (1981)].

Measurements of, and in particular on-line measurements of, the properties of coal are required for a range of industrial processes, for example:

(1) when coal is used as a fuel in thermal power plants;
(2) coal gasification;
(3) coal liquefaction;
(4) coking of coal;
(5) production of aluminium smelter anodes; and
(6) when coal is used for technological purposes e.g. in blast furnaces for steel production and for synthetic chemical production.

Information on the properties of coal is of most value if it is available immediately, since the information can then be used to optimize coincident use of processing of the coal. Nuclear techniques such as gamma ray absorption or neutron absorption and/or scattering have been used to measure the average atomic number of coal and infer from such measurements calorific value, carbon, hydrogen, ash and moisture content of coal on-line, for example, on conveyor belts. Nuclear on-line techniques have not been very valuable in practice, however, because they are not suitable for use with low density suspensions of coal in gas streams and are sensitive to small variations in the concentration of high atomic number impurities such as iron pyrites and clays. Nuclear techniques in general provide informaiton about elemental concentrations whereas the present invention is not limited to measurement of elemental concentrations but also provides information on the concentrations of molecular species. The usefulness of on-line measurements of coal is particularly apparent from the results of on-line capacitance measurements of coal which have provided reliable moisture content measurements. But on-line capacitance measurements of coal are limited, generally speaking, to the determination of moisture. Fourier transform infrared reflectance spectroscopy has been used to measure calorific value, carbon, hydrogen, ash and moisture content of coal using a sample by-line, however, the sampling technique is elaborate and sampling techniques are generally subject to error due to non-representative sampling. None of the aforementioned techniques measure the percentage of volatiles and the degree of surface oxidation rapidly enough to permit real time optimisation.

The standard methods [Standards Association of Australia, "Methods for the analysis and testing of coal and coke", AS 1038, 1981] for determining coal properties such as volatiles, carbon, hydrogen, moisture, ash and mineral contents involve collecting samples of the coal and then heating those samples of coal in furnaces in prescribed ways, measuring the gases produced and exampling the residue. The standard procedures are time consuming and the results obtained apply only to the actual sample. Those results are then inferred for the coal from which the sample was obtained. To provide confidence in the results obtained by these prior methods the sampling procedure must be demonstrably unbiassed which, in practice, is not a simple task [Standards Association of Australia, "Sampling of solid mineral fuels", AS 2646, 1984].

Microscopic techniques such as vitrinite reflectance and fluorescence microscopy have been used to determine certain coal properties.

Standard reflectance measurements require that the coal samples be optically polished and free from scratches. (See for example, "Coal Structure", ed. by Robert A. Meyers, Academic Press 1982). Complicated sampling and crushing techniques are employed before the coal samples are prepared in the form of polished blocks or polished briquets. Vitrinite reflectance is regarded as a standard microscopic technique for examining coal and is described in detail in Australian Standard AS 2486, "Microscopical determination of the reflectance of coal macerals, 1981". It has a nubmer of advantages over the use of microscopic fluorescence including:

(i) it is simpler;
(ii) standards for reflectance measurements are readily available;
(iii) reflectance values are much greater than fluorescence yields.

Reflectance studies therefore require lower fluences and are not subject to irreversible photochemical reactions.

However reflectance microscopy is not a technique readily adaptable for on-line measurements of coal properties. Standard reflectance measurements are performed on polished surfaces. On-line coal does not have polished surfaces, only a variety of particle sizes (lumps to fine particles) which provide scattering surfaces at a multitude of orientations to the incident radiation. Since reflectance is strongly orientation dependent and the on-line samples are not polished, reliable on-line reflectance measurements cannot be obtained.

A maceral is a microscopically recognizable organic constituent of coal which originated from the remains of different organs and tissues of plants, acquiring its present properties during peat accumulation and coalification. As a result of various studies of coal macerals using mciroscopic fluorescence, they have been grouped into several general maceral types, each of which is characterized by the intensity and spectral distribution of its fluorescence and by the rate at which the fluorescence fades when the maceral is illuminated.

Fluorescence microscopy has been shown to be a useful quantitative laboratory technique for determining the kinds and relative amounts of fluorescent macerals in various coals (see J. C. Crelling and D. F. Bensley, "Characterization of Coal Macerals by Fluorescence Microscopy", Chapter 3 in "Chemistry and Characterization of Coal Macerals" ACS Symposium Series 252 edited by R. E. Winans and J. E. Crelling, American Chemical Society, 1984). However fluorescence microscopy is not a standard technique and has severe limitations:

(1) it cannot be readily adapted to on-line measurements;
(2) rigorous sampling procedures must be adhered to;
(3) coal samplers are typically fixed in a block of resin and polished before microscopic analysis;
(4) fluorescence microscopy has been used to analyze individual coal macerals so that several hundred measurements must be made on any given sample in an attempt to obtain an unbiassed result;
(5) in fluorescence microscopy the sample areas examined are very small, being of the order of a few square microns;
(6) the entire range of coals (peat to anthracite) cannot be examined using fluorescence microscopy (M. Teichmuller and B. Durand, Int. J. of Coal Geol. 2, p. 197, 1983).
(7) the technique requires a highly skilled operator and is very subjective.

Thus, fluorescence techniques for measuring properties of coal have been generally considered to be techniques useful in the laboratory and heretofore have not been considered to be likely to lead to practical industrial on-line characterization of bulk coals.

It is an object of this invention to provide an apparatus for providing an output signal which is quantitatively related to a property of bulk coal and a method for quantitatively measuring a property of bulk coal.

Surprisingly the present inventors have found that the intensity of and the wavelengths present in the fluorescence emissions of bulk samples of coal which are irradiated by ultraviolet laser light are very sensitive to variations in the composition of the coal and are not confounded by sample size, presentation or ash content.

According to a first embodiment of this invention there is provided an apparatus for providing an output signal which is quantitatively related to a property of bulk coal the apparatus comprising a light source disposed to illuminate the coal, a fluorescence detector positioned in the path of fluorescence light emitted by the coal after interaction of light emitted by the source with the coal and measuring means associated with and/or coupled to the detector for measuring the intensities of the fluorescence light in selected wavelength region(s) and for deriving an output signal or signals quantitatively related to a property of the coal from the intensities.

According to a second embodiment of this invention there is provided a method for quantiatively measuring a property of bulk coal the method comprising:
(a) illuminating the coal with light;
(b) detecting in selected wavelength region(s) the fluorescence of the coal resulting from the illumination;
(c) determining the intensity or intensities of the fluorescence ratio of intensities of two selected wavelength regions of the fluorescence; and
(d) determining a property of bulk coal from the intensity or from the ratio.

The coal can be disposed on a conveyor belt, in a borehole, on the surface of a bore core, in a stockpile heap, at a mine face or can be suspended in a fluid stream.

This invention finds particular application in measuring the following properties of coal:

Rank, vitrinite reflectance, atomic H/C ratio, carbon, hydrogen and volatile contents, degree of surface oxidation, calorific value, coke yield, Gieseler initial softening temperature, Gieseler resolidification temperature, Gieseler maximum fluidity temperature and Dilatometer maximum dilatation temperature.

Preferably the apparatus of the first embodiment also includes calculating means associated with and/or coupled to the measuring means for calculating quantitative properties of bulk coal from the output signal. The calculating means can be a computer which integrates the intensities of the output signal within a selected wavelength region and compares the integrated value with a standard value for a given coal. Alternatively the calculating means can be an electronic integrating circuit. Other methods of calculating bulk properties of coal from the output signal can also be used such as comparing the intensities of the output signal within a first selected wavelength region with the output signal within a second selected wavelength region.

Preferably the method of the second embodiment also includes calculating quantitative properties of bulk coal from the output signal or signals.

Conveniently the light source is an ultraviolet light source in the wavelength range 180 nm–450 nm and may be an incoherent source such as an arc, arc lamp such as a Hg arc lamp or Xenon arc lamp $\chi$ or electrical plasma discharge or a coherent source such as a laser. A particularly preferred light source is a KrF laser (249 nm) due to its high power, reliability and relatively favorable atmospheric transmission. A XeCl laser (308 nm) is also a suitable light source due to its lower running costs and larger maintenance interval over a KrF laser.

Other ultraviolet lasers may be used in conjunction with or in place of a KrF or XeCl laser to provide additional or alternate ultraviolet wavelengths. These lasers may include but are not limited to KrCl, XeF, He-Cd, ArF, rare gas halide lasers, ultraviolet nitrogen lasers, ultraviolet noble gas lasers, frequency multiplied dye, ruby or neodymium lasers. Conveniently a modulated light source such as pulsed KrF laser (pulse preferably <100 nsec frequency 0–20 kHz) can be used. In another preferred form the intensity and/or wavelength of light from a continuous light source is modulated with, for example a Kerr cell, a Pockels cell or a chopper positioned between the light source and the coal.

Typically the modulated light is sampled for intensity, spatial and temporal variation before illuminating the coal to be analyzed. The sampler can be a single detector or an array of detectors adapted to discriminate in terms of wavelength and/or temporal variation. The remainder of the modulated light is passed through filters and/or a single monochromator to attenuate extraneous emissions at wavelengths remote from that of the primary laser wavelength. The size of the spot of the filtered modulated light directed onto target coal surface is typically controlled by a lens or lenses. The means of directing the ultraviolet light at the target coal surface depends on the type of the surface being studied and the medium in which it is immersed. Preferably the irradiation path and the field of view of the fluorescence detector are arranged to minimize the direct reflection of light from the source into the fluoresence detector.

The light intercepted by the coal surface may be reflected with its wavelength unmodified, or may be absorbed by the surface of the coal where it may be converted to heat, may chemically or physically modify the surface or it may excite the surface to fluoresce, emitting light at other wavelengths. The organic content of the coal causes the coal surface to fluoresce preferentially in the blue, close to the wavelength of the irradiating light.

The fluorescing coal surface is preferably viewed by a double monochromator optical filter designed to provide very high reflection of wavelenghts other than that to which it is tuned. This allows the fluoresecence behavior to be studied at wavelengths very close to that of the laser and prevents scattered laser light from obliterating the response when the filter is tune to wavelengths remote from that of the laser.

The light output of the double monochromator is detected by a fluorescence detector such as a photomultiplier, conveniently a fast response photomultiplier, and its intensity dependence on wavelength and temporal variation is subsequently measured and analyzed.

In another preferred form of the invention the laser is adjusted to produce polarized light and the fluorescence detector is adapted to discriminate between light with the original polarization vector and light with the orthogonal polarization vector. The major proportion of the specularly reflected laser light will retain its original polarization vector whereas the fluorescence emissions will be randomly polarized. A fluorescence detector with polarization analysis capability can be adjusted to preferentially accept orthogonally polarized light and thus discriminate against the scattered laser light.

The selected wavelength region(s) is typically a selected wavelength region(s) between 200 nm and 1000 nm preferably between 390 nm and 630 nm and more preferably is selected from the group consisting of 390–430 nm, 430–500 nm, 500–570 nm and 570–630 nm.

In another preferred form of the invention the coal surface is viewed through a bandpass filter or filter assembly which passes light in a selected wavelength range or sequence of wavelength ranges as the filter assembly is adjusted.

Optical fluorescence may be accompanied by a gradual reduction in the ability of the surface to fluoresce when stimulated by further optical illumination beyond a certain excitation intensity. At low excitation levels this reduction process may be imperceptible but may become rapid and obvious at higher fluences. This progressive fading of fluorescence is termed "alteration" and is used by petrographers in fluorescence microscopy to provide additional information about individual macerals. Mineral matter is usually much less subject to alteration than is the organic matter. This differing behavior provides an additional method of discriminating between mineral and organic matter.

Thus in a further preferred form of the invention variations in alteration are produced by changing the optical flux density of the incident light or by changing the time of illumination of the coal by the incident light to provide measurement of the bulk properties of coal.

This invention is not comparable with the established petrographic technique of the examination of polished sections of coal by reflectance and fluorescence microscopies since these techniques do not examine coal samples in bulk, are performed manually by a trained petrographer and not by an automatic instrument and, are not suited to operation with unprepared samples on conveyor belts or suspended in gas or liquid streams.

This invention preferably uses a very narrow wavelength range source of light. This band of narrow wavelengths allows this invention to examine poorly fluorescing bulk coal without the measurement system being overloaded by scattered source light which, if the wavelength range of the source were not narrow, could contain substantial energy in the same wavelength range as the desired fluorescence.

In contrast to the prior art, this invention produces data radiply [a single measurement can be made in under a second] and is therefore suitable for on-line analysis and may examine a much larger quantity of the material being characterized. If necessary all of the coal can be examined. The results are immediately and continuously available. In this respect the present invention has the same advantages as nucleonic and microwave systems which perform on-line analysis of coal for ash and for moisture content but which cannot measure % volatile matter or rank. Further, the process of the present invention does not use radioactive materials. In addition the process of the present invention determines the properties of bulk coal directly from fluorescence spectra.

A preferred embodimemt of this invention and examples of this invention will now be described with reference to the following drawings in which:

FIG. 3($b$) is a fluorescence intensity vs wavelength spectrum of coal from a Liddell seam (Australia) using an $N_2$ laser (337 nm) excitation source.

FIG. 7($b$) is a plot of the integrated fluorescence intensity vs wavelength curves in the blue spectral region. ($A_{blue}$) vs % volatile matter DAFB for coal suite 2.

FIG. 9($b$) is a plot of $A_{blue}$ vs atomic H/C ratio for coal suite 2.

Figure 1:
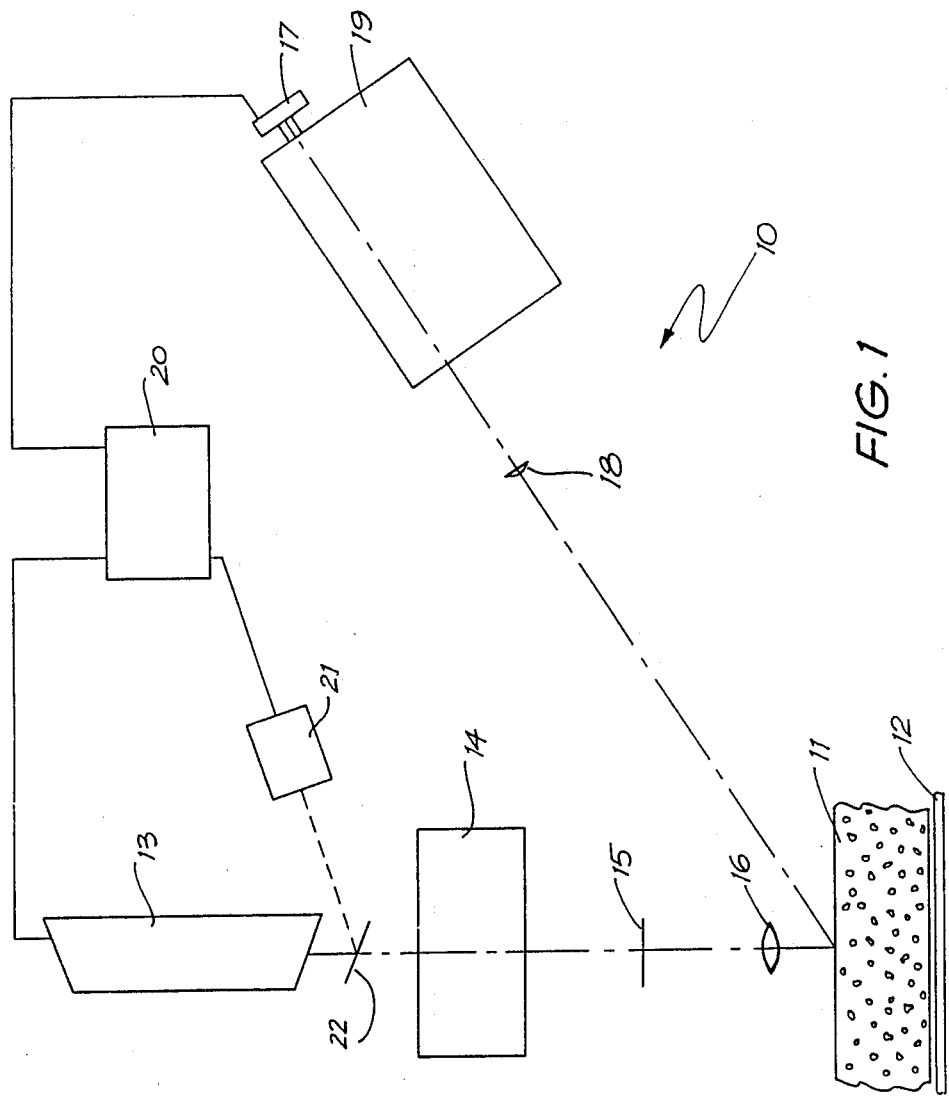
FIG. 1 is a schematic diagram of a system for determining properties of coal.

Referring to FIG. 1 a system 10 for quantitatively measuring properties of bulk coal 11 on conveyor 12 includes a pulsed nitrogen laser 13 (wavelength=337 nm, pulselength less than 10 nsec, frequency 0.1-75 Hz. peak power maximum 1M Watt) from which laser light is directed onto coal 11 via filteres and/or single monochromator 14 and aperture 15 and lens 16. A portion of the laser light is sampled by photodiode 21 via beam splitter 22. Photodiode 21 generates a reference signal which is directed to electronic detection system 20. Filters and/or single monochromator 14 attenuate extraneous emissions of wavelengths remote from that of the primary laser wavelength (337 nm) and the area of the laser beam which illuminates coal 11 is controlled by the characteristics of lens 16. In practice the higher the power output of laser 13 the larger the area to which the beam can be expanded. Lens 18 is positioned to avoid receiving substantial refleted light from coal 11 into double monochromator 19 which selects a range of wavelengths which are then detected by fast response photomultiplier 17. Electronic measuring system 20 associated with laser 13, photodiode 21 and photomultiplier 17 is used to measure the intensities of the detected fluorescence spectrum and provide output signals which are proportional to the intensities to plot intensity vs wavelenglth curves which are integrated and/or ratioed in/at selected wavelength regions and used to calculate properties of bulk coal.

In use laser 13 directs a pulse of laser light at coal 11 on conveyor 12 via filters and monochromator 14, aperture 15 and lens 16. The resultant intensity of fluorescence vs wavelength spectrum emanating from coal 11 is detected by photomultiplier 17 via lens 18 and double monochromator 19.

The intensity of the detected spectrum is then measured by electronic detection system 20 and properties of coal 11 are determined by comparing areas under the resultant fluorescence intensity curves in selected wavelength regions with standard plots for the particular type of coal 11. Alternatively properties of coal 11 can be determined by the ratio which is defined as the ratio of fluorescence intensity at a wavelenglth X divided by the fluorescence intensity at a wavelength Y or by using the fluorescence intensity at the maximum wavelength.

Figure 2:
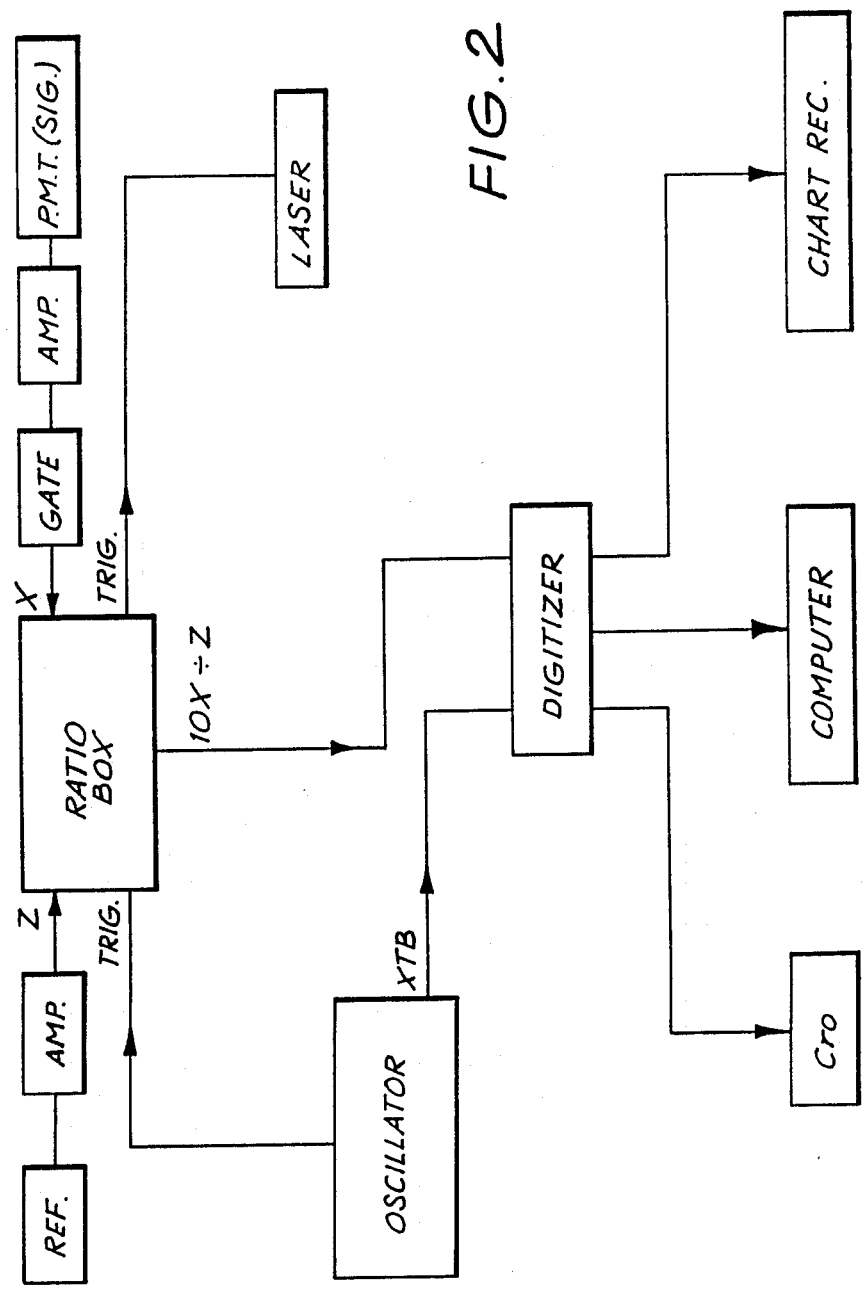
FIG. 2 is a schematic diagram of an electronic detection system for use in the system of FIG. 1.

As shown in FIG. 2 the photomultiplier and reference detector pulses can be amplified and filtered via nuclear pulse amplifiers (Hewlett Packard 5582A) with 1 μs integration and 5 μs differentiation times. The signal-to-noise ratio can be enhanced by gating the amplifier output of the signal channel. An electronic ratio box stretches both the gated signal and reference amplifier outputs and ratios the stretched pulses. The ratio can then be digitized with a Biomation 805 digitizer. A master oscillator controls the laser pulse rate and clocks the digitizer so that one digitzed ratio is available for each laser shot. The output of the digitizer is displayed on a CRO or chart recorder and stored by microcomputer for subsequent processing.

Properties of bulk coal which have been measured by the apparatus and method of this invention and are now discussed under separate headings with reference to the Figures.

Fixed and Total Carbon Content

In many practical application it is essential to determine carbon content of coal accurately.

Typically total carbon content is determined by an analytical laboratory technique which involves combusting a sample of coal and measuring liberated $CO_2$. Typically fixed carbon is determined by heating a sample of coal under specified conditions and at a specified rate and such analysis is usually conducted in the laboratory.

Figure 4:
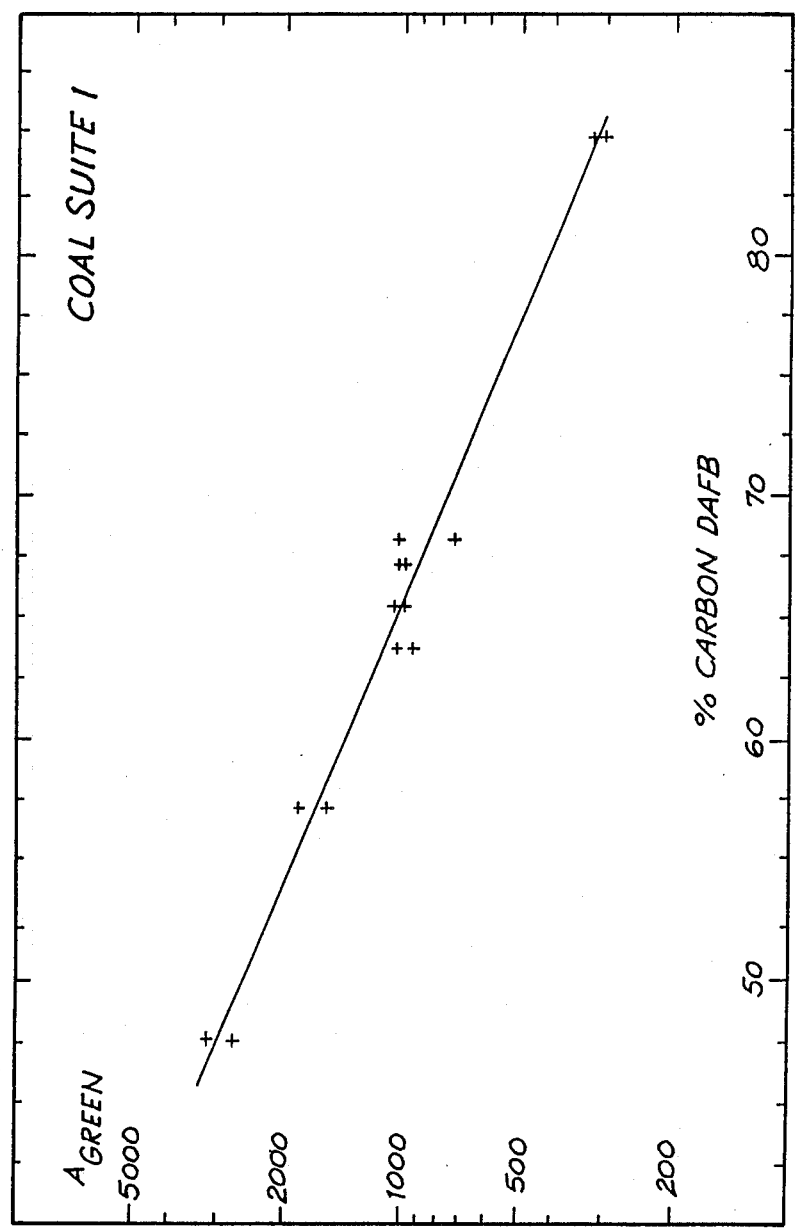
FIG. 4 is a plot of Area under fluorescence intensity vs wavelength curves in the green spectral region (500–570 nm), ($A_{green}$) vs % carbon DAFB for coal suite 1. (DAFB means dry ash free basis).
Figure 5:
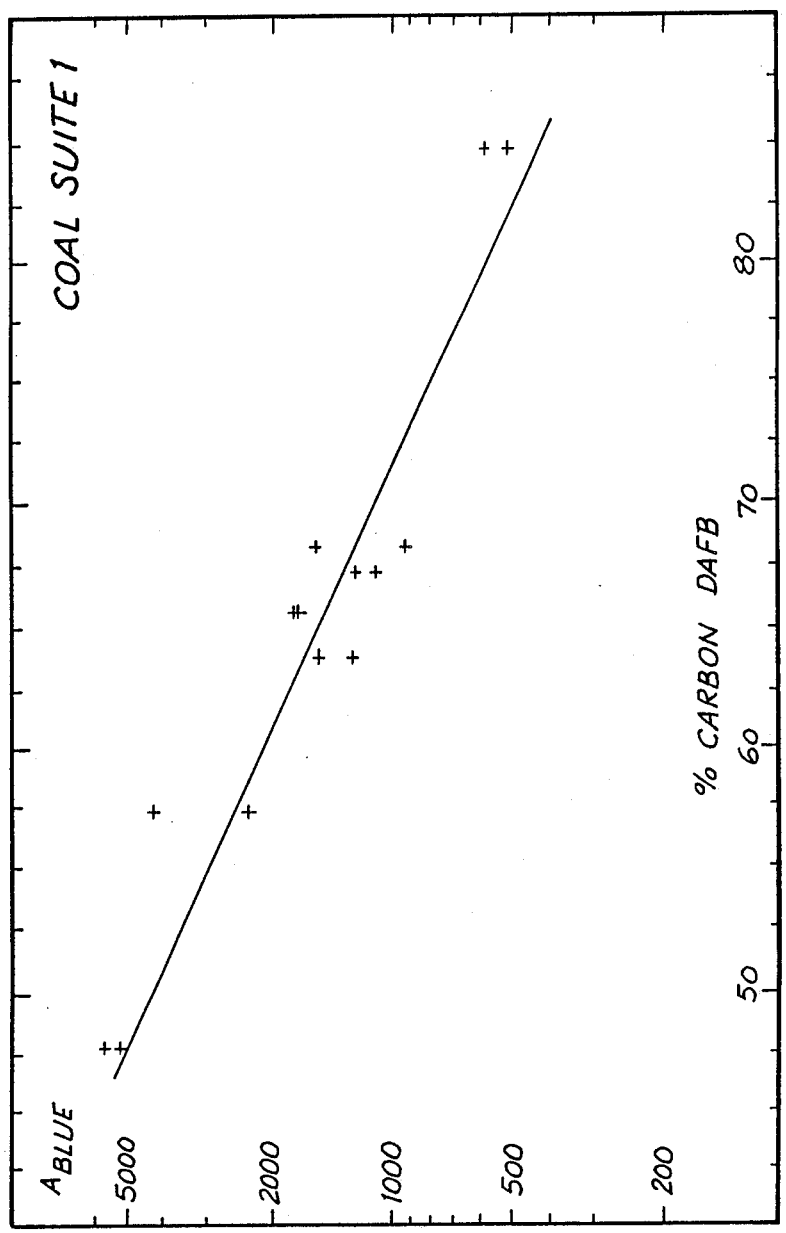
FIG. 5 is a plot of the integrated fluorescence intensity vs wavelength curves in the blue spectral region (430–500 nm), ($A_{blue}$) vs % carbon DAFB for coal suite 1.
Figure 8:
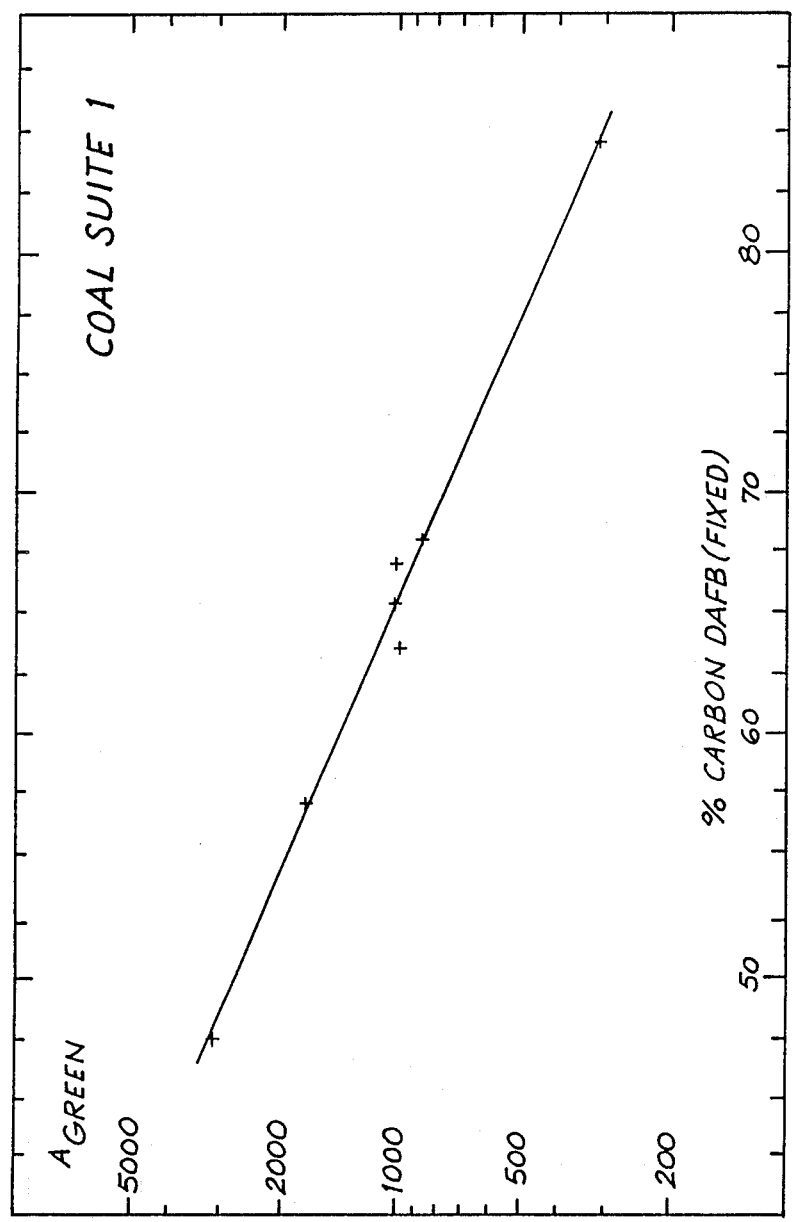
FIG. 8 is a plot of $A_{green}$ vs % carbon DAFB for coal suite 1 made by statistically averaging the points of FIG. 4.

FIGS. 4, 5 and 8 which show correlations of fixed carbon content with fluorescence intensity demonstrate that it is possible to predict with relative accuracy fixed carbon content in coal using the method of the invention.

Similarly it is possible to predict with relative accuracy total carbon content in coal using the method of the invention.

Volatile Matter

Figure 6:
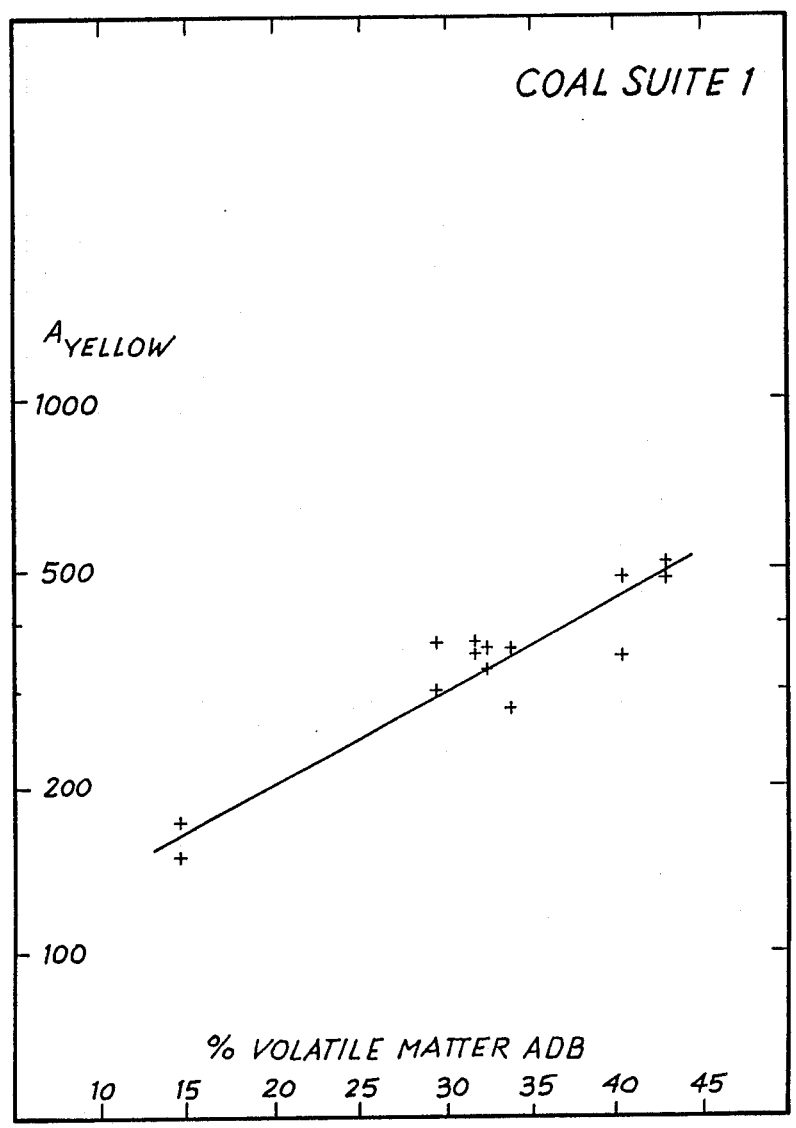
FIG. 6 is a plot of Area under fluoresence intensity vs wavelength curves in the yellow spectral region (570–630 nm), ($A_{yellow}$) vs % volatile matter ADB for coal suite 1. (ADB means air dried bais).
Figure 7A:
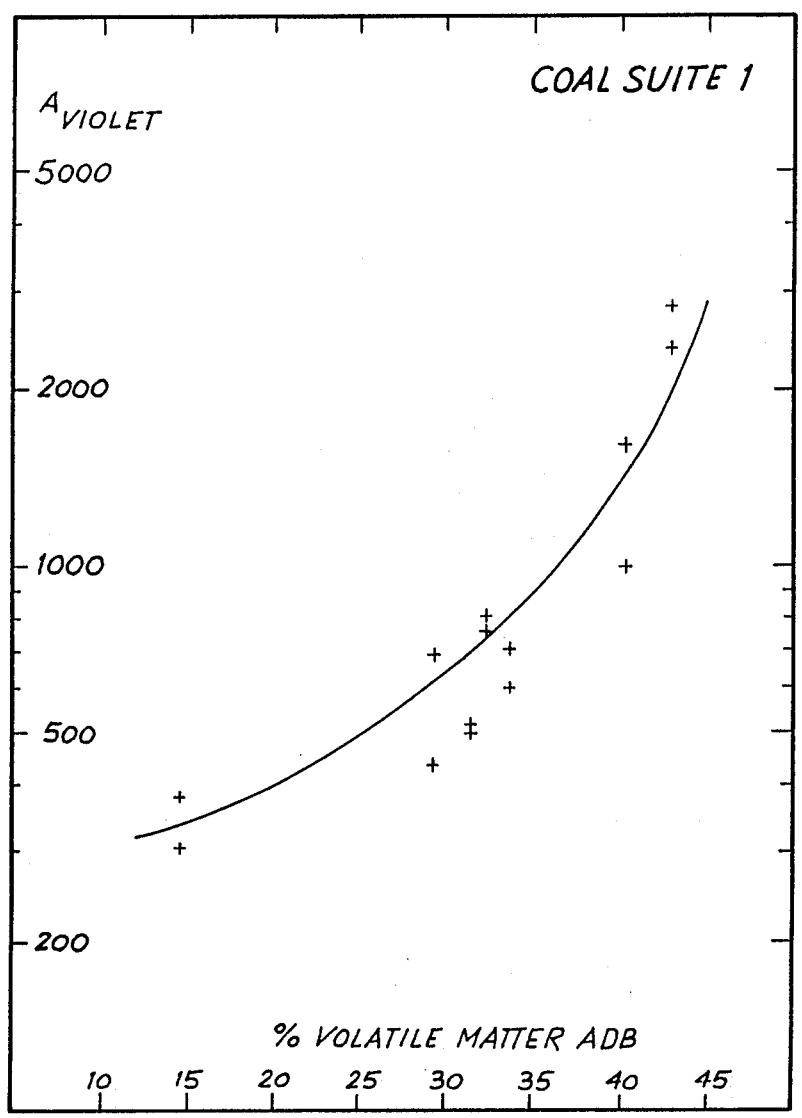
FIG. 7($a$) is a plot of Area under fluorescence intensity vs wavelength curves in the violet spectral region (390–430 nm), ($A_{violet}$) vs % volatile matter ADB for coal suite 1.
Figure 7B:
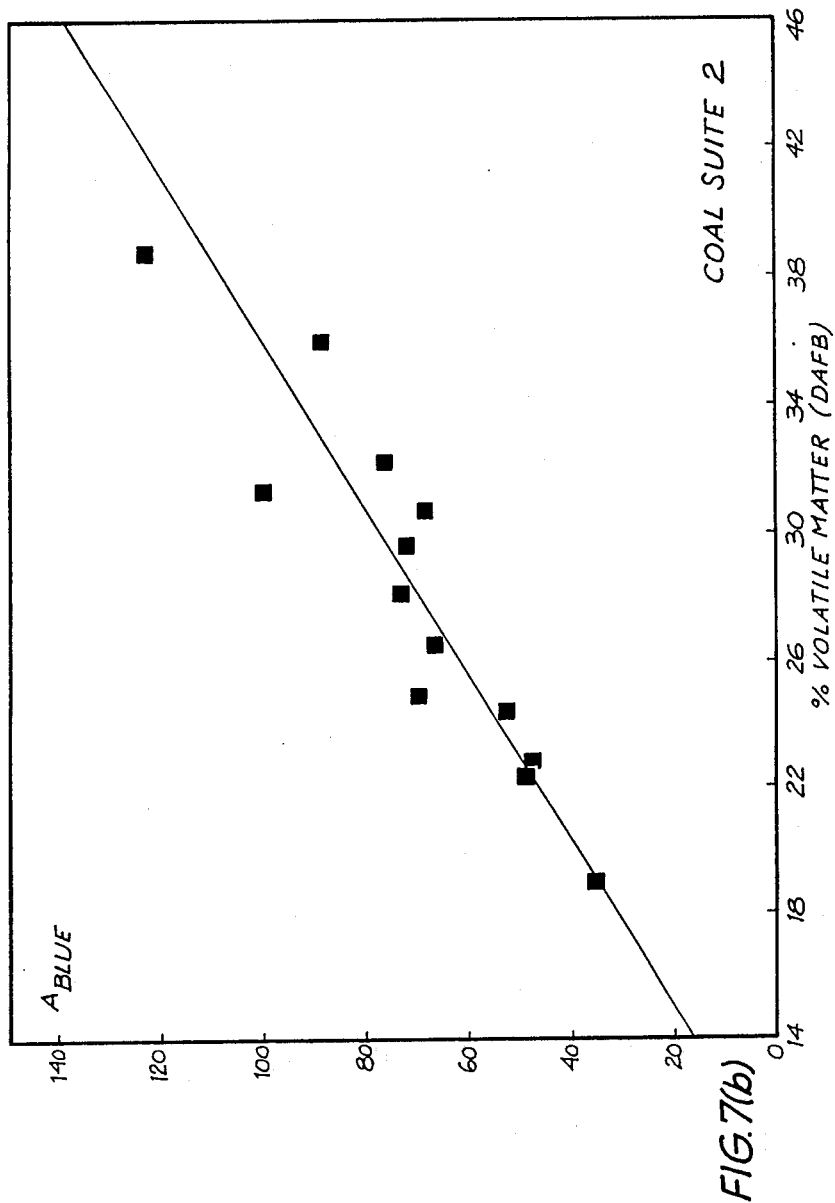

Volatile matter is used as a basis for evaluating the suitability of coals for combusion and carbonization. FIGS. 6, 7(a) and 7(b) show plots of yellow, violet and blue area versus percentage volatile matter ADB, ADB and DAFB respectively. It is evident that a good correlation is obtained (particularly FIG. 7(b)) and it is apparent that percentage volatile matter can be determined by the method of the invention.

Atomic Hydrogen to Carbon Ratio

Figure 9A:
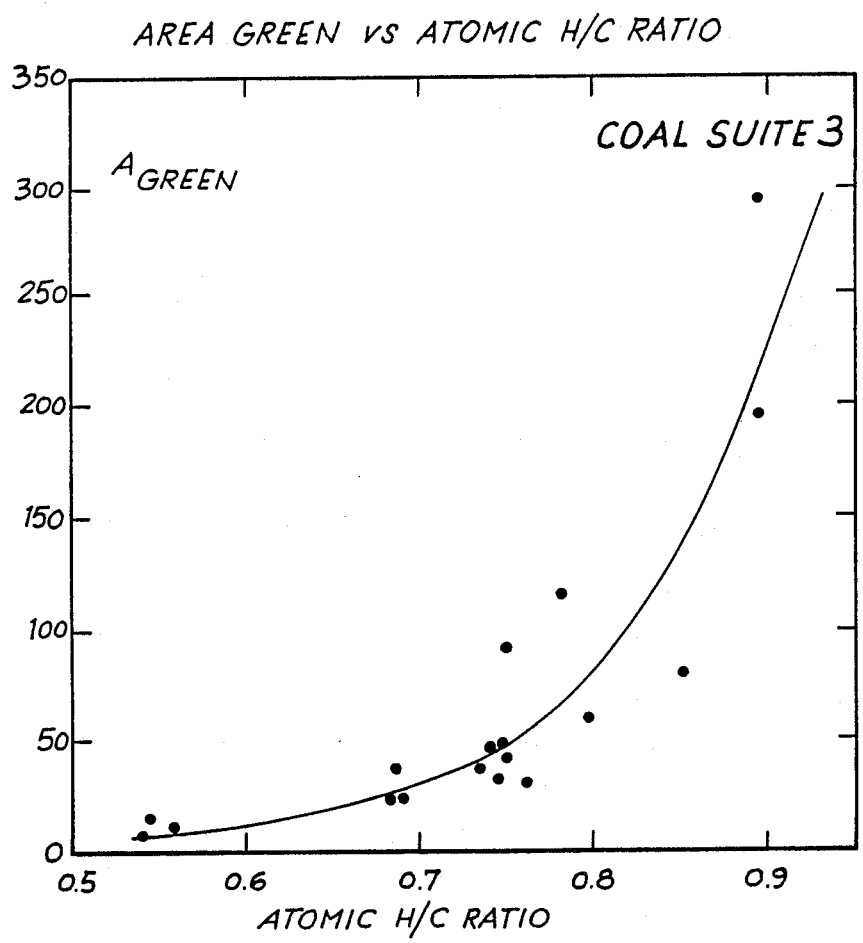
FIG. 9($a$) is a plot of $A_{green}$ vs atomic H/C ratio DAFB for coal suite 3.
Figure 9B:
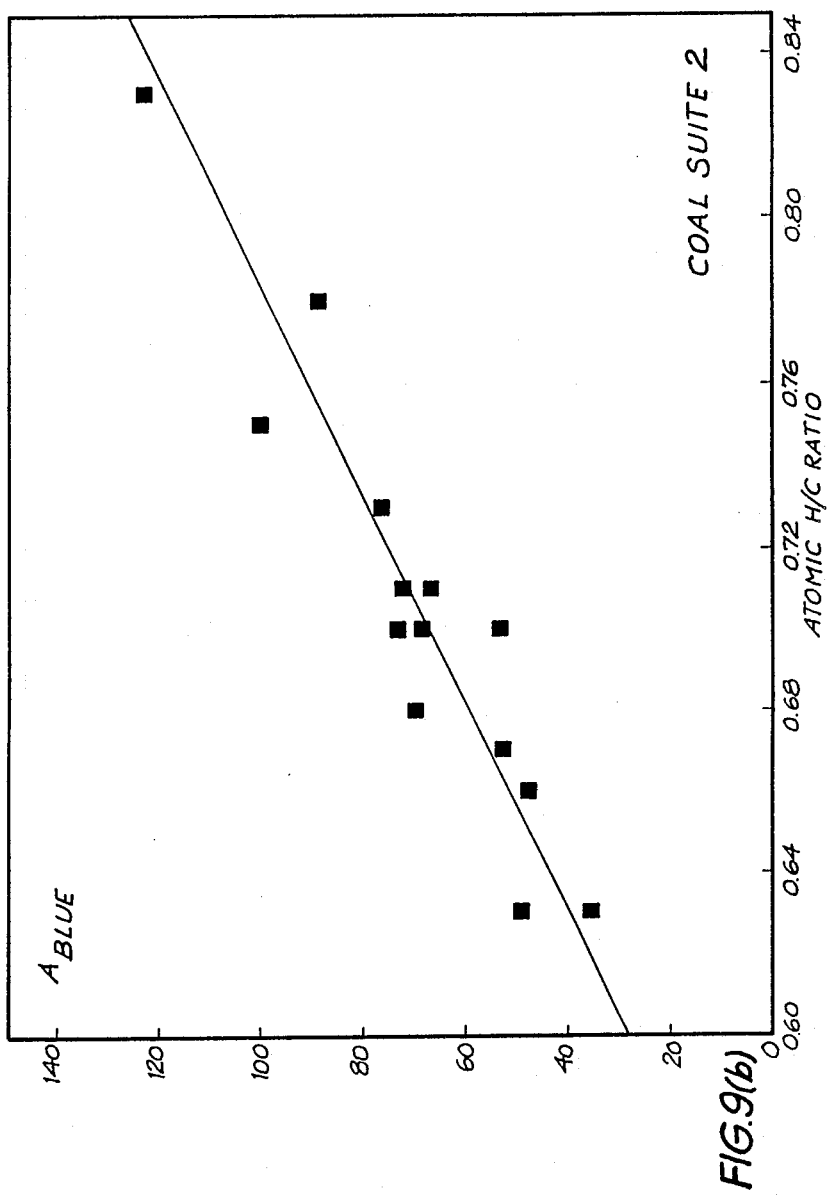

The carbon content of coal increases and the hydrogen content decreases during coalification so that the atomic H/C ratio can be used to determine the rank of a coal sample. The rank determines the suitability of the coal for coking and for combustion. FIGS. 9(a) and (b) show plots of green area and blue area versus atomic H/C ratio respectively for two different suites of coal. It is apparent from these Figures that a good correlation is obtained and that the method of the invention can be used to determine coal rank.

Vitrinite Reflectance

Figure 10A:
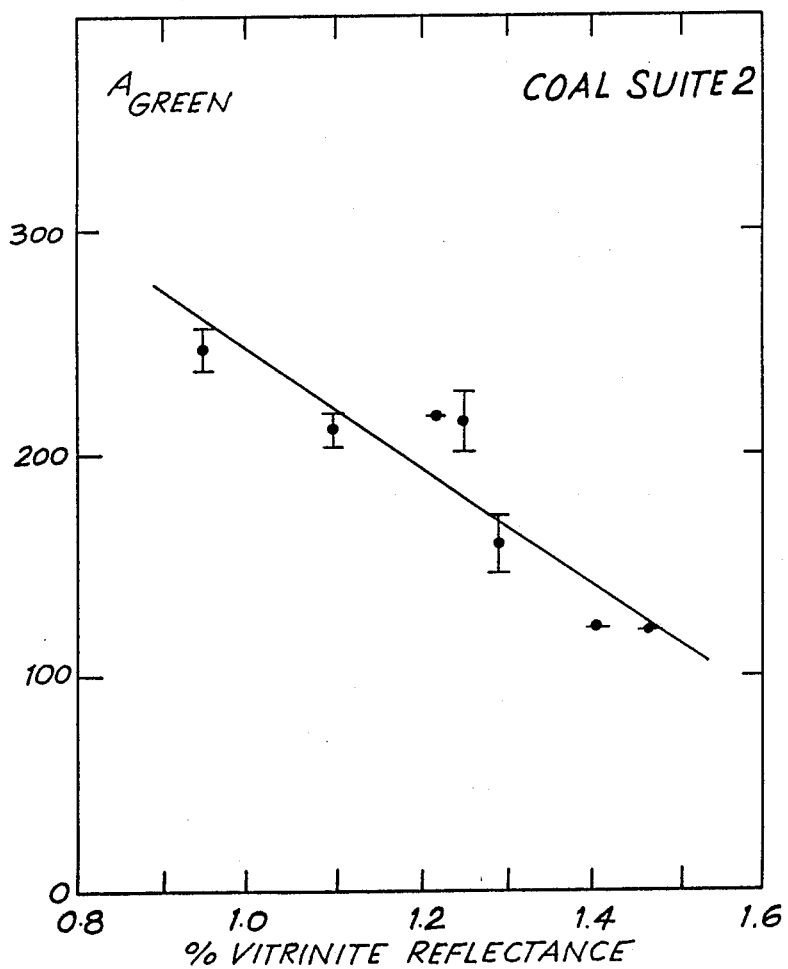
FIG. 10($a$) is a plot of $A_{green}$ vs % vitrinite reflectance for coal suite 2.
FIG. 10(b) is a plot of $A_{blue}$ vs % vitrinite reflectance for coal suite 2.

Vitrinite reflectance is one of the standard methods for determining coal rank. FIGS. 10(a) and (b) show plots of green area and blue area fluorescence intensities versus vitrinite reflectance respectively for the same suite of coal. It is apparent from these Figures that a good correlation is obtained and that coal rank can be determined using this method of the invention.

Alteration

Figure 11:
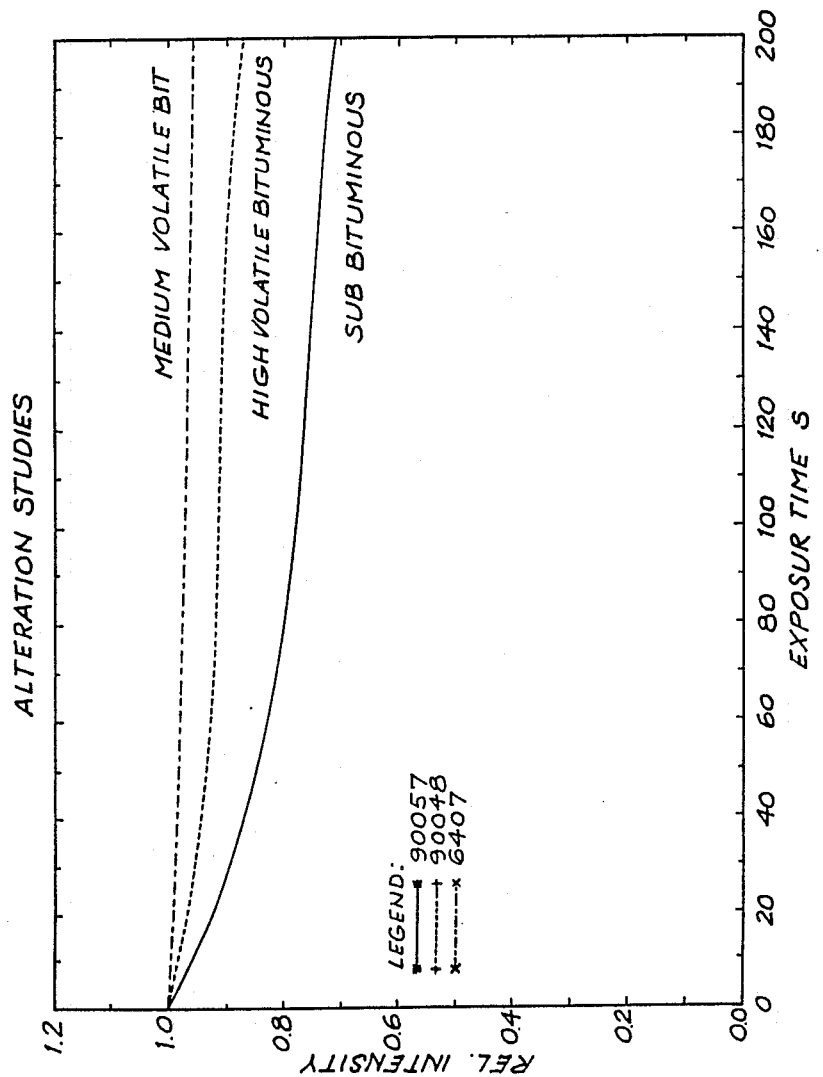
FIG. 11 is a plot of relative fluorescence intensity at 450 nm vs time of exposure to laser flux for three coals.

Alteration is defined as the fading of the fluorescence intensity with prolonged illumination. FIG. 11 shows plots of fluorescence intensity versus exposure time for three different types of coals. It is evident from this Figure that the different types of coals can be distinguished from plots of this type by the differing alterations.

Coke Yield

Figure 12:
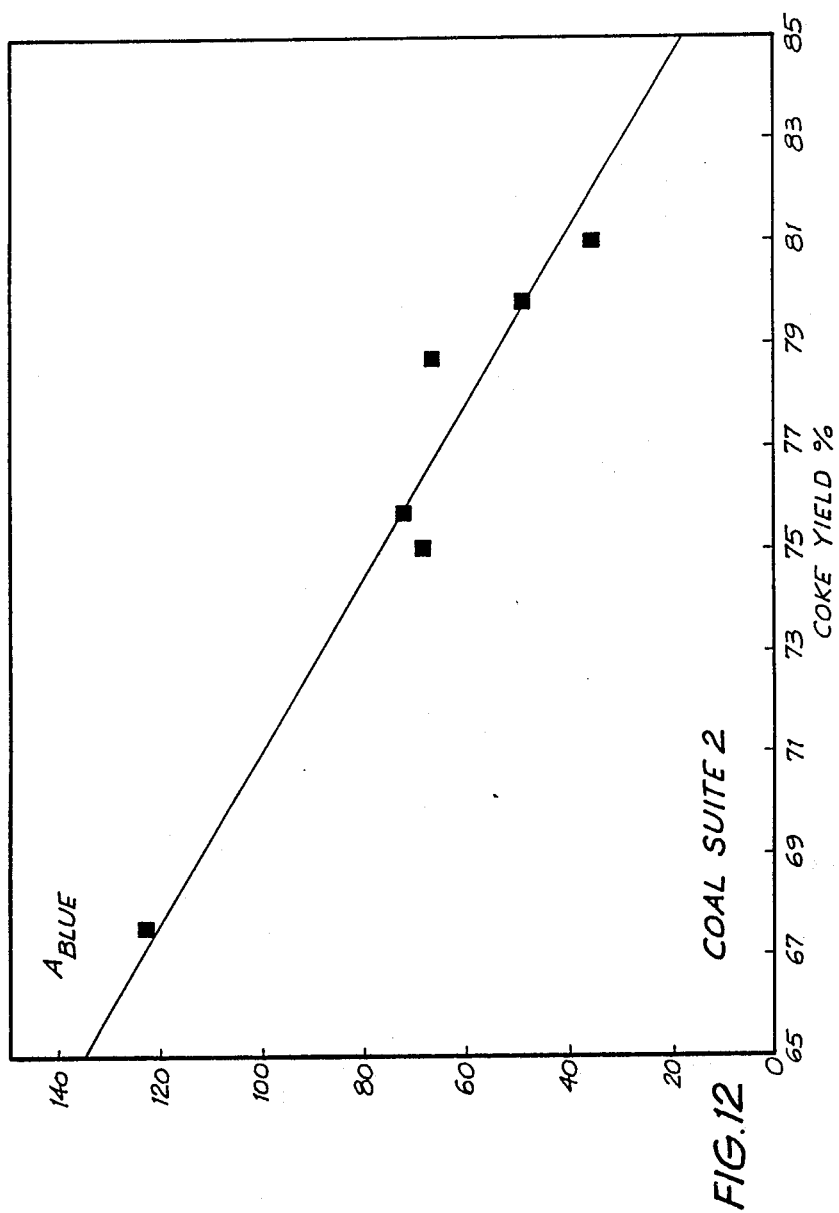
FIG. 12 is a plot of $A_{blue}$ vs % coke yield for the selected coking coals of Table 2.

Coke yield is understood to be the amount of coke which can be derived from a given sample of coal. FIG. 12 shows a plot of fluorescence intensity vs coke yield for suite 2 coals. It is evident from this Figure that percentage coke yield can be determined by the method of the invention.

Maximum dilatation temperature

Figure 13:
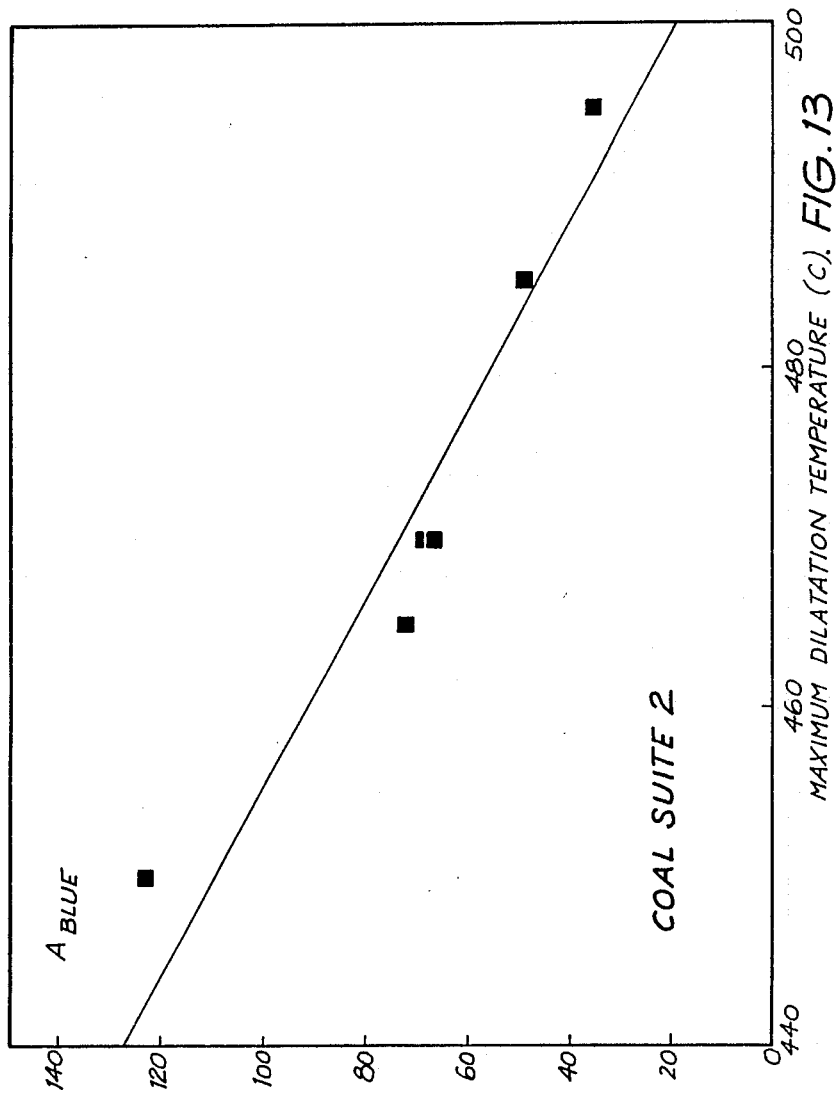
FIG. 13 is a plot of $A_{blue}$ vs the Maximum dilatation Temperature (degree C.) for the selected coking coals of Table 2.

The swelling properties of a coal are determined by a standard dilatation test. The FIG. 13 shows the temperature of maximum swelling (maximum dilatation temperature) correlates well with blue area of fluorescence intensity.

Gieseler resolidification temperature

Figure 14:
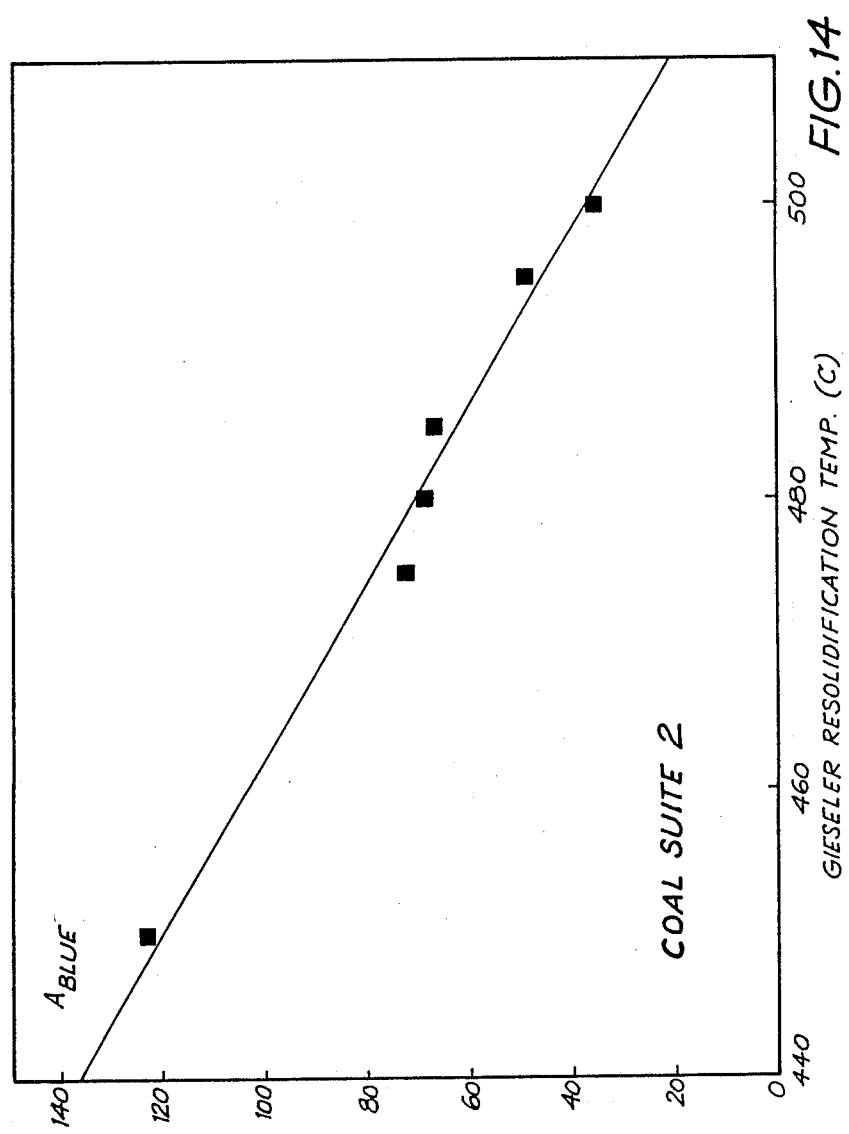
FIG. 14 is a plot of $A_{blue}$ vs Gieseler Resolidification Temperature (degrees C.) for the selected coking coals of Table 2.

The thermoplastic properties of a coal are characterized by the Gieseler fluidity test. FIG. 14 shows a good correlation between the Gieseler resolidification temperature and the blue area of fluorescence intensity.

Accuracy

The reproducibility of the fluorescence intensity data approaches that of most of the supplied data. The scatter could be greatly reduced by illuminating a larger area of the coal with each laser pulse or by sweeping the laser beam over the coal sample and averaging the spectrum over the larger area. The laser data is the average of 3–9 measurements and has a standard deviation of =<10%. The dynamic range of the data is however larger than that of conventional parameters which usually don't vary by more than a factor of ten. Australian Standards [Standards Association of Australia AS 1038 part 16, "Methods for the analysis and testing of coal and coke-reporting of results", (1981)] specify the repeatability and reproducibility of the standard methods of Proximate and Ultimate analysis, but not the accuracy. Quoted reproducibilities vary depending upon the actual moisture, ash and volatile contents but are in the range 0.1% to 0.3% absolute, and up to 0.5% for ash content of high ash coals. The specified probable errors of 0.06% (absolute) in the vitrinite reflectance data (see FIGS. 10(a) and 10(b)) could greatly influence the correlation. A few of the standard tests require some subjectivity on the part of the operator which can influence the accurancy obtained. The present invention is not influenced by operator subjectivity.

The practice of this invention will now be illustrated by the following examples.

EXAMPLE 1

Intensity of fluorescence vs wavelength spectra were measured for various types of coal from two suites and areas under the fluorescence intensity curves were determined in the following selected spectral regions in accordance with the apparatus and method above except two separate samples of each coal were examined in order to test reproducibility. The second suite was freshly characterized. The coal was initially ground to a fine powder which was tipped into a standard 3 cm aluminium X-ray fluorescence cup and pressed into a solid biscuit.

$A_{violet}$ is defined as the area under the curve lying between 390–430 nm.

$A_{blue}$ is defined as the area under the curve lying between 430–500 nm.

$A_{green}$ is defined as the area under the curve lying between 500–570 nm.

$A_{yellow}$ is defined as the area under the curve lying between 570–630 nm.

Figure 3A:
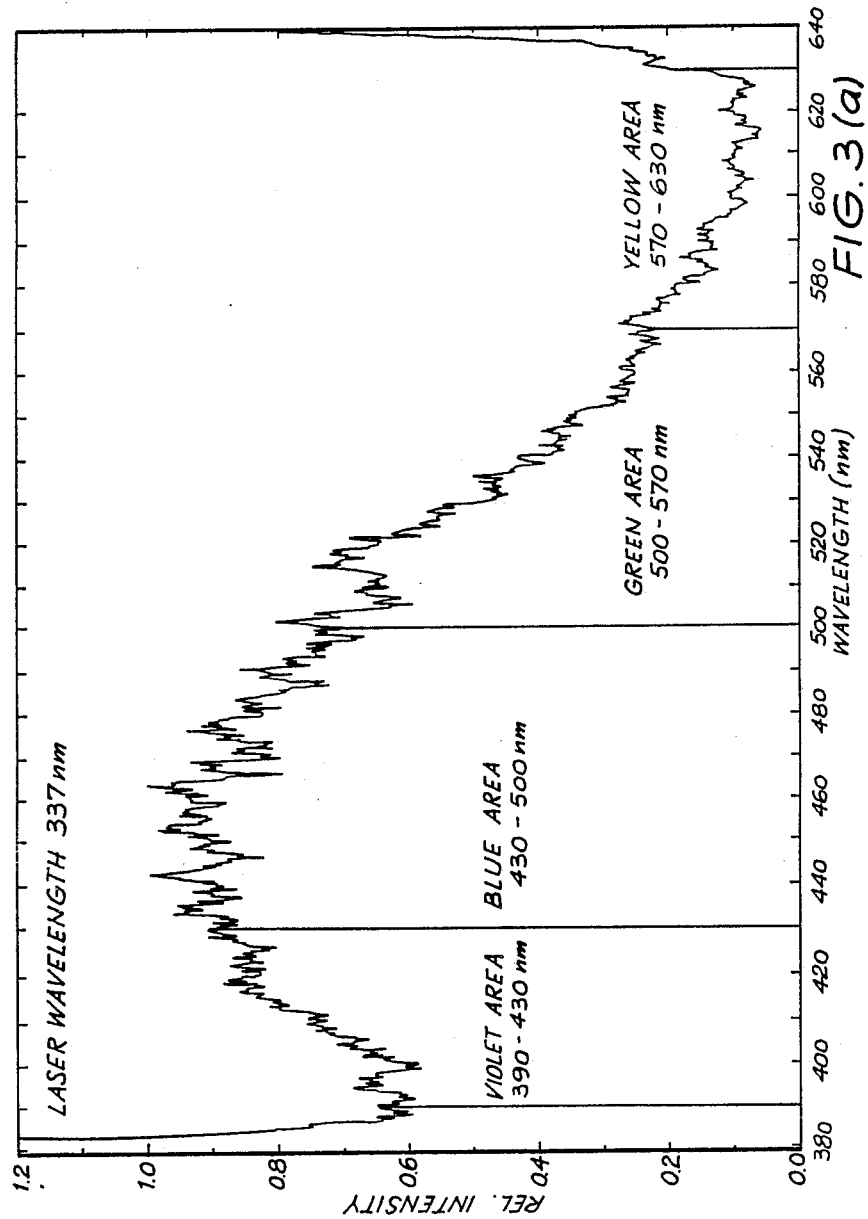
FIG. 3($a$) is a fluorescence intensity vs wavelength spectrum of coal from an Anglesea seam (Australia) using an $N_2$ laser (337 nm) excitation source.

Typical intensity of fluorescence vs wavelength curves are illustrated in FIGS. 3(a) and 3(b). The intensity of the fluorescence vs wavelength curves is then integrated over the violet, blue, green and yellow spectral regions defined above. The data is then compared with standard calibration curves to determine the required characteristic of the coal. Standard calibration curves can be obtained by applying the method of the invention to samples of coal in which the desired parameter is already known accurately. By plotting a fluorescence parameter against the known parameter a working curve is obtaining from which unknown parameters can be determined once the unknowns fluorescence has been characterized by the method of the invention.

Alteration can be determined by examining the fluorescence at a single wavelength. The fluorescence intensity that is measured is then compared with the fluorescence intensity obtained after a predefined period of illumination. Alternatively the fluorescence intensity can be monitored throughout the period of illumination and an intensity vs time profile can be derived and which depends on the type of coal being examined [see FIG. 11].

A number of typical parameters for the vitrinite rich coals of suite 1 are listed in Table 1. Vitrinite reflectance data for the coals of suite 2 is listed in Table 2. The data in the tables has been obtained by applying the standard methods of analysis according to Australian Standard AS 1038.

EXAMPLE 2

If the coals examined are restricted to those possessing caking properties, those that exhibit a physical change when subjected to the influence of heat, then information may be gained about the suitability of the coal for coke production. Fluorescence vs wavelength spectra were measured for the following coking coals of suite 2: 6842, 6843, 6844, 6845, 6846, 6847. The integrated fluorescence intensities were determined for the spectral regions in accordance with the apparatus and method above except 1 to 4 separate samples of each coal were examined and each sample was measured 3 times, being rotated approx. 45 degrees between measurements. FIGS. 12–14 illustrate some of the correlations that may be obtained. Plotting $A_{blue}$ against coke yield, Maximum dilatation temperature and Gieseler resolidification temperature yields $R^2$ correlation coefficients of 0.94, 0.91 and 0.98 respectively.

TABLE 1

| SAMPLE NUMBER | SEAM | % FIXED CARBON DAFB | SUITE 1 H/C ATOMIC RATIO | % VOL MATTER ADB | FLUORESCENCE PARAMETERS (ARBITRARY UNITS) | | | |
|---|---|---|---|---|---|---|---|---|
| | | | | | $A_{violet}$ | $A_{blue}$ | $A_{green}$ | $A_{yellow}$ |
| 90039 | ANGLESEA | 47.8 | 0.779 | 42.9 | 2886 | 5657 | 3029 | 514 |
| | | | | | 2421 | 5136 | 2700 | 493 |

TABLE 1-continued

| | | SUITE 1 | | | | | | |
|---|---|---|---|---|---|---|---|---|
| SAMPLE NUMBER | SEAM | % FIXED CARBON DAFB | H/C ATOMIC RATIO | % VOL MATTER ADB | \multicolumn{4}{c}{FLUORESCENCE PARAMETERS (ARBITRARY UNITS)} |
| | | | | | $A_{violet}$ | $A_{blue}$ | $A_{green}$ | $A_{yellow}$ |
| 90041 | GRETA | 57.3 | 0.849 | 40.3 | 1643 | 4186 | 1814 | 357 |
| | | | | | 1007 | 2271 | 1561 | 500 |
| 90042 | ECLIPSE | 67.2 | 0.744 | 31.7 | 507 | 1225 | 968 | 357 |
| | | | | | 521 | 1121 | 1009 | 364 |
| 90044 | WRIGHT | 65.7 | 0.737 | 32.3 | 768 | 1746 | 1036 | 368 |
| | | | | | 821 | 1739 | 975 | 336 |
| 90049 | EXCEL | 84.8 | 0.570 | 14.7 | 304 | 514 | 320 | 152 |
| | | | | | 377 | 584 | 302 | 173 |
| 90052 | FIERY | 68.4 | 0.739 | 29.4 | 443 | 930 | 732 | 305 |
| | | | | | 704 | 1557 | 1014 | 368 |
| 90054 | YOUNG WALLSEND | 63.8 | 0.757 | 33.8 | 611 | 1252 | 939 | 286 |
| | | | | | 718 | 1514 | 1025 | 364 |

TABLE 2

| | | | SUITE 2 | | | | |
|---|---|---|---|---|---|---|---|
| SAMPLE | % VOLATILE MATTER DAFB | % MEAN MAX VITRIMITE REFLECTANCE | COKE YIELD % | MAXIMUM DILATATION TEMP (°C.) | GIESELER RESOLIDIFICATION TEMPERATURE (°C.) | $A_{blue}$ arbitrary units | $A_{green}$ arbitrary units |
| 6407 | 31.3 | 1.08 | — | — | — | 100 | — |
| 6533 | 32.2 | 1.10 | — | — | — | 76 | 211 |
| 6535 | 35.9 | 0.95 | — | — | — | 89 | 247 |
| 6536 | 22.8 | 1.46 | — | — | — | 48 | 122 |
| 6538 | 24.9 | 1.25 | — | — | — | 70 | 214 |
| 6539 | 28.1 | 1.22 | — | — | — | 73 | 218 |
| 6540 | 24.4 | 1.29 | — | — | — | 52 | 165 |
| 6711 | 24.3 | 1.40 | — | — | — | 53 | 122 |
| 6842 | 26.5 | 1.16 | — | 470 | 485 | 67 | — |
| 6843 | 29.6 | 1.80 | 78.7 | 465 | 475 | 72 | — |
| 6844 | 38.7 | 0.77 | 67.5 | 450 | 450 | 123 | — |
| 6845 | 18.9 | 1.58 | 81.0 | 495 | 500 | 35 | — |
| 6846 | 22.3 | 1.30 | 79.8 | 485 | 495 | 49 | — |
| 4847 | 30.7 | 1.02 | 75.0 | 470 | 480 | 68 | — |

TABLE 3

| | SUITE 3 | | |
|---|---|---|---|
| SAMPLE NUMBER | SEAM | ATOMIC H/C RATIO | $A_{green}$ (arbitrary units) |
| 90039 | ANGLESEA | 0.779 | 118 |
| 90040 | WONGAWILLI | 0.544 | 15 |
| 90041 | GRETA | 0.849 | 80 |
| 90042 | ECLIPSE | 0.744 | 50 |
| 90043 | WONGAWILLI | 0.691 | 24 |
| 90044 | WRIGHT | 0.737 | 49 |
| 90045 | TANTIVY | 0.732 | 39 |
| 90046 | LIDDELL | 0.794 | 59 |
| 90047 | WALLOON | 0.895 | 195 |
| 90048 | BERGINS | 0.749 | 93 |
| 90049 | EXCEL | 0.570 | 13 |
| 90050 | DAWSON | 0.539 | 8 |
| 90051 | STRIPED BACON | 0.747 | 42 |
| 90052 | FIERY | 0.739 | 33 |
| 90053 | CALLIDE | 0.684 | 38 |
| 90054 | YOUNG WALLSEND | 0.757 | 32 |
| 90055 | LEIGH CREEK | 0.682 | 24 |
| 90056 | STOCKTON BLOCK | 0.748 | 44 |
| 90057 | COMMODORE | 0.894 | 297 |

What we claim is:

1. An apparatus for determining quantitatively a property of bulk coal from a fluorescence spectrum resulting from UV illumination of said coal, said apparatus comprising:

a UV light source for illuminating a plurality of surface macerals of bulk coal with UV light;

a fluorescent light detector positionable for detecting fluorescent light emitted by said macerals of said bulk coal in response to said illumination and for deriving output signals amplitude related to intensities of said detected fluorescent light as a function of wavelengths of said detected fluorescent light, and;

calculating means operatively associated with said detector for calculating quantitatively a property of said bulk coal from said output signals said calculating means comprising;

integration means integrating said output signals within a selected wavelength region for providing at least one integrated value; and comparing means comparing said integrated value with at least one standard value derived from a calibration study of coal whereby to indicate quantitatively said property of said bulk coal from said comparison.

2. The apparatus as defined in claim 1 wherein: said detector is positionable for detecting fluorescent light emitted by said macerals of said bulk coal in response to period of illumination of said macerals and for deriving output signals amplitude related to intensities of said detected fluorescent light as a function of wavelengths of said detected fluorescent light and of period of illumination of said bulk coal; and wherein said integration means integrating said output signals within a selected wavelength region as a function of wavelengths of said detected fluorescent light and of period of illumination of said bulk coal for providing at least one integrated value.

3. The apparatus as defined in claim 1 wherein: said detector is positionable for detecting fluorescent light emitted by said macerals of said bulk coal in at least one selected wavelength region as a function of integrated energy flux incident on said bulk coal and for deriving output signals amplitude related to intensities of said detected fluorescent light as a function of integrated energy flux incident on said bulk coal; and wherein said integration means integrating said output signals within a selected wavelength region as a function of integrated energy flux incident on said bulk coal to provide at least one integrated value.

4. The apparatus as defined in claim 1 wherein the light source is selected from the group consisting of Hg arc lamp, Xenon arc lamp, KrF laser, XeCl laser, He-Cd laser, ArF laser, UV $N_2$ laser, frequency multiplied dye laser, ruby laser and neodymium laser.

5. The apparatus as defined in claim 1 further including means to modulate the intensity of light emitted by said light source associated with and/or coupled to said light source and wherein said detector detects modulated fluorescent light emitted by said macerals in selected wavelength region(s).

6. The apparatus as defined in claim 1 further including modulating means disposed between said light source and said bulk coal to modulate the intensity of light emitted by said light source prior to illumination of said bulk coal and wherein said detector detects modulated fluorescent light emitted by said macerals in selected wavelength region(s).

7. The apparatus as defined in claim 1 wherein said light source is a laser producing polarized light and said detector discriminates between polarized light and originating from said laser and fluorescent light with an orthogonal polarization vector to the light originating from the laser, in order to differentiate between fluorescent light emitted by said macerals and light scattered by said bulk coal.

8. The apparatus as defined in claim 1 wherein the selected wavelength region(s) is a selected wavelength region(s) between 200 nm and 1000 nm.

9. The apparatus as defined in claim 1 wherein the selected wavelength region(s) is a selected wavelength region(s) between 390 nm and 630 nm.

10. The apparatus as defined in claim 1 wherein the selected wavelength region(s) is selected from the group consisting of 390-430 nm, 430-500 nm, 500-570 nm and 570-630 nm.

11. The apparatus as defined in claim 1 wherein said property of said bulk coal is selected from the group consisting of rank, vitrinite reflectance, atomic H/C ratio, carbon, hydrogen and volatile contents, degree of surface oxidation, calorific value, coke yield, Gieseler initial softening temperature, Gieseler resolidification temperature, Gieseler maximum fluidity temperature and Dilatometer maximum dilatation temperature.

12. The apparatus as defined in claim 1 wherein the UV light emitted by the UV light source is in the range 180 nm-450 nm.

13. An apparatus for determining quantitatively a property of bulk coal from a fluorescence spectrum resulting from UV illumination of said coal, said apparatus comprising:

a UV light source for illuminating a plurality of surface macerals of said bulk coal with UV light;

a fluorescent light detector positionable for detecting fluorescent light emitted by said macerals of said bulk coal in response to said illumination and for deriving output signals amplitude related to intensities of said detected fluorescent light as a function of wavelengths of said detected fluorescent light; and calculating means operatively associated with said detector for calculating quantitatively a property of said bulk coal from said output signals said calculating means comprising:

ratioing means ratioing said output signals within a first selected wavelength region with said output signals within a second selected wavelength region to provide a ratioed value; and comparing means comparing said ratioed value with at least one standard value derived from a calibration study of coal whereby to indicate quantitatively said property of said bulk coal from said comparison.

14. The apparatus as defined in claim 13 further including means to modulate the intensity of light emitted by said light source associated with and/or coupled to said light source and wherein said detector detects modulated fluorescent light emitted by said macerals in selected wavelength region(s).

15. The apparatus as defined in claim 13 further including modulating means disposed between said light source and said bulk coal to modulate the intensity of light emitted by said light source prior to illumination of said macerals and wherein said detector detects modulated fluorescent light emitted by said macerals in selected wavelength region(s).

16. The apparatus as defined in claim 13 wherein said light source is a laser producing polarized light and said detector discriminates between polarized light originating from said laser and fluorescent light with an orthogonal polarization vector to the light originating from the laser, in order to differentiate between fluorescent light emitted by said macerals and light scattered by said bulk coal.

17. The apparatus as defined in claim 13 wherein the selected wavelength region(s) is a selected wavelength region(s) between 200 nm and 1000 nm.

18. The apparatus as defined in claim 13 wherein the selected wavelength region(s) is a selected wavelength region(s) between 390 nm and 630 nm.

19. The apparatus as defined in claim 13 wherein the selected wavelength region(s) is selected from the group consisting of 390-430 nm, 430-500 nm, 500-570 nm and 570-630 nm.

20. The apparatus as defined in claim 13 wherein said property of said bulk coal is selected from the group consisting of rank, vitrinite reflectance, atomic H/C ratio, carbon, hydrogen and volatile contents, degree of surface oxidation, calorific value, coke yield, Gieseler initial softening temperature, Gieseler resolidification temperature, Gieseler maximum fluidity temperature and Dilatometer maximum dilatation temperature.

21. The apparatus as defined in claim 13 wherein the UV light emitted by the UV light source is in the range 180 nm-450 nm.

22. A method for quantitatively measuring a property of bulk coal from a fluorescence spectrum resulting from UV illumination of said coal, said method comprising:

(a) illuminating a plurality of surface macerals of said bulk coal with UV light;

(b) detecting fluorescent light emitted by said macerals of said bulk coal in response to said illuminating;

(c) deriving output signals amplitude related to the intensities of said detected fluorescent light as a funciton of wavelength;

(d) calculating quantitatively a property of said bulk coal from said output signals by:
   integrating said output signals within a selected wavelength region to provide at least one integrated value; and
   comparing said integrated value with at least one standard value derived from a calibration study of coal whereby to indicate quantitatively said property of said bulk coal from said comparison.

23. The method as defined in claim 22 wherein said light is derived from a light source selected from the group consisting of Hg arc lamp, Xenon arc lamp, KrF laser, XeCl laser, He-Cd laser, ArF laser, UV $N_2$ laser, frequency multiplied dye laser, ruby laser and neodymium laser.

24. The method as defined in claim 22 further including:
   modulating the intensity of said UV light;
   deriving output signals amplitude related to the intensities of detected modulated fluorescent light emitted by said macerals in selected wavelength region(s).

25. The method as defined in claim 22 comprising illuminating said macerals with light from a laser producing polarized light and deriving output signals amplitude related to the intensities of orthogonally polarized fluorescent light emitted by said macerals to differentiate between fluorescent light emitted by said macerals and light scattered by said bulk coal.

26. The method as defined in claim 22 wherein the selected wavelength region(s) is a selected wavelength region(s) between 200 nm and 1000 nm.

27. The method as defined in claim 22 wherein the selected wavelength region(s) is a selected wavelength region(s) between 390 nm and 630 nm.

28. The method as defined in claim 22 wherein the selected wavelength region(s) is selected from the group consisting of 390–430 nm, 430–500 nm, 500–570 nm and 570–630 nm.

29. The method as defined in claim 22 wherein said property of said bulk coal is selected from the group consisting of rank, vitrinite reflectance, atomic H/C ratio, carbon, hydrogen and volatile contents, degree of surface oxidation, calorific value, coke yield, Gieseler initial softening temperature, Gieseler resolidification temperature, Gieseler maximum fluidity temperature and Dilatometer maximum dilatation temperature.

30. The method as defined in claim 22 wherein said bulk coal is disposed on a conveyor belt, in a borehole, on the surface of a bore core, in a stockpile heap, at a mine face or is suspended in a fluid stream.

31. The method as defined in claim 22 wherein the UV light is in the range 180 nm–450 nm.

32. A method for quantitatively measuring a property of bulk coal from a fluorescence spectrum resulting from UV illumination of said coal, said method comprising:
   (a) illuminating a plurality of surface macerals of said bulk coal with UV light;
   (b) detecting fluorescent light emitted by said macerals of said bulk coal in response to said illuminating;
   (c) deriving output signals amplitude related to the intensities of said detected fluorescent light as a function of wavelength;
   (d) calculating quantitatively a property of said bulk coal from said output signals by:
      ratioing said output signals within a first selected wavelength region with said output signals within a second selected wavelength region to provide a ratioed value; and
      comparing the ratioed value with at least one standard value derived from a calibration study of coal whereby to indicate said bulk coal from said comparison.

33. The method as defined in claim 32 wherein said light is derived from a light source selected from the group consisting of Hg arc lamp, Xenon arc lamp, KrF laser, XeCl laser, He-Cd laser, ArF laser, UV $N_2$ laser, frequency multiplied dye laser, ruby laser and neodymium laser.

34. The method as defined in claim 32 further including:
   modulating the intensity of said UV light, deriving output signals amplitude related to the intensities of detected modulated fluorescent light emitted by said macerals in selected wavelength region(s).

35. The method as defined in claim 34 comprising illuminating said macerals with light from a laser producing polarized light and deriving output signals amplitude related to the intensities of orthogonally polarized fluorescent light emitted by said macerals to differentiate between fluorescent light emitted by said macerals and light scattered by said bulk coal.

36. The method as defined in claim 32 wherein the selected wavelength region(s) is a selected wavelength region(s) between 200 nm and 1000 nm.

37. The method as defined in claim 32 wherein the selected wavelength region(s) is a selected wavelength region(s) between 390 nm and 630 nm.

38. The method as defined in claim 32 wherein the selected wavelength region(s) is selected from the group consisting of 390–430 nm, 430–500 nm, 500–570 nm and 570–630 nm.

39. The method as defined in claim 37 wherein said property of said bulk coal is selected from the group consisting of rank, vitrinite reflectance, atomic H/C ratio, carbon, hydrogen and volatile contents, degree of surface oxidation, calorific value, coke yield, Gieseler initial softening temperature, Gieseler resolidification temperature, Gieseler maximum fluidity temperature and Dilatometer maximum dilatation temperature.

40. The method as defined in claim 32 wherein said bulk coal is disposed on a conveyor belt, in a borehole, on the surface of a bore core, in a stockpile heap, at a mine face or is suspended in a fluid stream.

41. The method as defined in claim 32 wherein the UV light is in the range 180 nm–450 nm.

* * * * *